United States Patent
Kohno et al.

(10) Patent No.: US 7,642,401 B2
(45) Date of Patent: Jan. 5, 2010

(54) DIABETES MODEL ANIMAL

(75) Inventors: Kenji Kohno, Nara (JP); Pedro Herrera, Chene-Bourg (CH); Virginie Nepote, Annemasse (FR)

(73) Assignees: National University Corporation Nara Institute of Science and Technology, Nara (JP); University of Geneva, Geneva (CH)

( * ) Notice: Subject to any disclaimer, the term of this patent is extended or adjusted under 35 U.S.C. 154(b) by 197 days.

(21) Appl. No.: 11/815,014

(22) PCT Filed: Aug. 1, 2005

(86) PCT No.: PCT/JP2005/014476

§ 371 (c)(1),
(2), (4) Date: Jul. 29, 2007

(87) PCT Pub. No.: WO2006/080106

PCT Pub. Date: Aug. 3, 2006

(65) Prior Publication Data

US 2008/0320609 A1    Dec. 25, 2008

(30) Foreign Application Priority Data

Jan. 31, 2005    (JP) ............................. 2005-023668

(51) Int. Cl.
*A01K 67/027*    (2006.01)
*C12N 15/00*    (2006.01)
(52) U.S. Cl. .......................................... 800/18; 800/21
(58) Field of Classification Search ...................... 800/3, 800/8, 18, 21
See application file for complete search history.

(56) References Cited

U.S. PATENT DOCUMENTS 5,824,840 A *   10/1998   Seo et al. ....................... 800/9
6,576,813 B2    6/2003    Kohno

OTHER PUBLICATIONS

Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
Wagner (May 1995, Clin. and Experimental Hypertension, vol. 17, pp. 593-605).*
Mullins (1996, J. Clin. Invest., vol. 98, 1557-1560).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*

(Continued)

*Primary Examiner*—Michael C. Wilson
(74) *Attorney, Agent, or Firm*—Kirk Hahn

(57) ABSTRACT

We prepared a transgene comprising human HB-EGF precursor cDNA, as a diphtheria toxin receptor gene, at the downstream of an insulin promoter, and introduced this transgene into a mouse fertilized egg, to produce a transgenic mouse of the present invention. In this mouse, human HB-EGF precursors are expressed specifically in islet beta cells, and by injection of diphtheria toxin, islet beta cells are selectively destroyed, resulting in that the mouse shows diabetes two or three days after the injection. This mouse can be utilized in screening and development of new medicines and therapy protocols for diabetes.

4 Claims, 11 Drawing Sheets

OTHER PUBLICATIONS

Taurog, 1988, J. Immunol., vol. 141, p. 4020-4023.*

Kohno (Protein, Nucleic acid, Enzyme, 1998, vol. 43, No. 1, p. 11-24).*

Kohno, Kenji et al., Analyses of cell function using diphtheria toxin, Protein, Nucleic acid, Enzyme vol. 43, No. 1, pp. 11-24 (1998).

Fernandes A et al, Differentiation of new insulin-producing cells is induced by injury in adult pancreatic islets, 1997, Endocrinology, vol. 138, No. 4, p. 1750-1762.

Andre I et al, Checkpoints in the progression of autoimmune disease: Lessons from diabetes models., 1996, Proc Natl Acad Sci USA, vol. 93, No. 6, p. 2260-2263.

Saito M et al, Diphtheria toxin receptor-mediated conditional and targeted cell ablation in transgenic mice, 2001, Nat Biotechnol., vol. 19, No. 8, p. 746-750.

Holz A et al, Neither B lymphocytes nor antibodies directed against self antigens of the islets of langerhans are required for development of virus-induced autoimmune diabetes, 2000, J Immunol., vol. 165, No. 10, p. 5945-5953.

Garcia-Ocana A et al, Adenovirus-mediated hepatocyte growth factor expression in mouse islets improves pancreatic islet transplant performance and reduces beta cell death, 2003, J Biol Chem., vol. 278, No. 1, p. 343-351.

Pedro Herrera "Mastering a mouse model of inducible diabetes" Pole Position 2, Aug. 2004, p. 12.

* cited by examiner

Light Gray : Insulin
Dark Gray : Glucagon

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial
<220> FEATURE:
<223> OTHER INFORMATION: Primer designed for DNA amplification by PCR

<400> SEQUENCE: 1
tgcctgtctc ccagatcact gtg                                              23

<210> SEQ ID NO 2
<211> LENGTH: 22
<212> TYPE: DNA
<213> ORGANISM: Artificial
<220> FEATURE:
<223> OTHER INFORMATION: Primer designed for DNA amplification by PCR

<400> SEQUENCE: 2
ttcagcacca ccgacggcag ca                                               22
```

DIABETES MODEL ANIMAL

This application is the U.S. National Phase under 35 U.S.C. § 371 of International Application PCT Patent Application No. PCT/JP2005/014476, filed on Aug. 1, 2005, which claims priority to Japanese Patent Application No. 2005-023668, filed on Jan. 31, 2005. The contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a diabetes model animal, and more specifically, relates to (1) an inducible diabetes model animal, whose islet beta cells can be selectively destroyed by administration of a compound such as a diphtheria toxin, so that it is possible to induce a symptom of the diabetes at a desired time in the animal, (2) a method for generating such diabetes model animal and (3) a method for screening new medicines or therapy protocols for the diabetes, by use of such diabetes model animal.

BACKGROUND ART

Diabetes (diabetes mellitus) is one of very popular lifestyle-related diseases. In Japan now it is reported that six million people or more are suffering from the diabetes, and if the number of potential diabetes patients are added, there might be as many as 14 million diabetes patients. A symptom of the diabetes is characterized by continuous high concentration of blood glucose. One big problem is that the diabetes causes various other diseases (=complications) such as diabetic neuropathy, diabetic hypertonias and diabetic arteriosclerosis, in addition to diabetic blindness and urinemia.

The diabetes can be classified into two types. One is Type 1 diabetes, also called an insulin-dependent diabetes. The patient of Type 1 diabetes cannot secrete insulin because beta (β) cells in islet of Langerhans of pancreas (=islet beta cells), which are insulin producing and secreting cells, are destroyed due to autoimmunity or other reasons. Another is Type II diabetes, where secreted insulin doesn't work well. A typical patient of Type II diabetes is the person, whose insulin secretion is likely to decrease, additionally having the factor like obesity, mental stresses or shortage of physical activity.

The development of a diabetes model animal is very important, not only for the researches of the diabetes and its complications caused by the diabetes, but also for the development of new treatment and therapeutic agent for these diseases. So far some diabetes model animals are developed and used. Here, we explain typical two kinds of (Type I) diabetes model mice. One is a mouse which can be obtained by administrating the compound called streptozotocin that acts on specifically the islet beta cells, while the other is a mouse (NOD mouse) exhibiting a symptom similar to the diabetes, which can be established from a strain of mouse frequently having cataract.

Although the former mouse can be obtained by a simple procedure that is administration of the streptozotocin, there are problems in (1) efficiency and reproducibility to induce the diabetes and (2) side reaction to other organs and cells such as renal damages. The latter NOD mouse is thought to be suitable to the researches of the Type 1 diabetes because it resembles a symptom of the Type 1 diabetes. The problem of this model mouse is that (1) a long time rearing (breeding) is necessary (eight months or more rearing is necessary in order to develop the diabetes by 70-80%), and that (2) it is not predictable when it develops the diabetes, in addition to the problem that (3) there is male/female difference and this method is only applicable for the female mouse.

By the way, this inventor has developed an original method by which only a target cell group can be destroyed at a desired time, named TRECK (Toxin Receptor Mediated Cell Knockout) ("Protein, Nucleic acid, Enzyme" Vol. 43, No. 1, pp 11-24 (1998); Nature Biotechnology, Vol. 19, pp 746-750 (2001)). In fact, hepatic cells could be selectively destroyed using this method, i.e., by firstly producing a transgenic mouse with an expression unit including a diphtheria toxin receptor gene in the downstream of albumin enhancer/promoter which is a hepatic cell specific promoter, and then administrating a diphtheria toxin to this transgenic mouse (WO 98/33899; U.S. Pat. No. 6,576,813).

DISCLOSURE OF THE INVENTION

The object of the present invention is to provide a new diabetes model animal which can overcome the above-mentioned problems, more specifically, to provide a new diabetes model animal which can show a symptom of the diabetes at a desired time efficiently and promptly with no male/female difference, also having the benefit that there is little side reaction to any other organs and cells than the islet beta cells. Another object of the present invention is to provide a screening method of new medicines or therapy protocols for the diabetes by use of such diabetes model animal.

The inventors adopted the above-mentioned TRECK method and firstly produced transgenic mice expressing diphtheria toxin receptors specifically in the islet beta cells, and then diphtheria toxin was administrated to these mice, leading to the following findings that (1) in a few days after administration of the diphtheria toxin, islet beta cells of these mice were selectively destroyed and a symptom of hyperglycemia appeared, (2) their insulin concentration in blood decreased remarkably, with insulin production becoming low, while their blood glucose level was recovered by administration of insulin to a normal level, (3) there were differences in the survival rate of these mice, etc., depending on dosage (amount) of the diphtheria toxin. These findings led us to the present invention.

The present invention includes the following industrially and medically useful inventions A) to H).

A) An inducible diabetes model animal, produced by introducing an expression unit comprising a gene (DNA) encoding a receptor for a compound, which is substantially non-toxic to a wild type of the animal, under control of a promoter which functions specifically in islet beta (β) cells, so as to express the receptor specifically in those cells, wherein the animal shows glycemia (hyperglycemia) at a desired time by administrating the compound to the animal and selectively disrupting all or part of the islet beta cells of the animal.

Although the above-mentioned compound is essentially non-toxic to the model animal, but it is toxic to the islet beta cells expressing receptors for the compound. Therefore, the islet beta cells can be selectively destroyed by administrating a small amount of the compound to induce a symptom of the diabetes in the model animal, because the animal falls into the state of low insulin production (hypoinsulinism). It is not required that all of the islet beta cells are destroyed. A symptom of the diabetes can be also induced through destruction of part of those cells.

B) A diabetes model animal, whose islet beta cells are selectively disrupted, by administration of the compound to the diabetes model animal set forth in A) above, or its descendants.

Here, the word "descendants" means all the animals, where receptors for the compound are expressed specifically in the islet beta cells, that are born as progeny of first produced diabetes model animal, and they are not limited to progeny within several generations. The diabetes model animal can live for a long time even after showing glycemia, by adjusting dosage (amount) of the compound and therefore, it is possible to use the animal for a long time for various experiments or examinations, etc.

C) A diabetes model animal set forth in A) or B), wherein the promoter which functions specifically in islet beta cells is an insulin promoter.

It is preferable to use a human-, rat- or mouse-insulin promoter, but the insulin promoter is not limited to these promoters. Also, the length and the location of a used insulin promoter sequence are not limited, as long as it has promoter activity specifically in the islet beta cells.

D) A diabetes model animal set forth in A), B) or C), wherein the receptor is a diphtheria toxin receptor.

The mouse and the rat, etc. are essentially non-sensitive to a diphtheria toxin, whereas the human and the ape, etc. are sensitive to it. Therefore, by producing the model mouse (or the rat, etc.) so as to express diphtheria toxin receptors specifically in its islet beta cells which are insulin producing cells, and then administrating a diphtheria toxin at a desired time, only its islet beta cells are selectively destroyed, resulting in that the animal shows diabetes two or three days after the administration.

E) A diabetes model animal set forth in D), wherein the diphtheria toxin receptor is a human heparin-binding EGF-like growth factor (hHB-EGF) precursor.

The above human heparin-binding EGF-like growth factor (hHB-EGF) precursor is suitable as the diphtheria toxin receptor. However, other heparin-binding EGF-like growth factor (HB-EGF) precursors may be also used as the diphtheria toxin receptor; for example, HB-EGF precursors derived from other kinds of animal high-sensitive to the diphtheria toxin such as the ape, the hamster and the guinea pig.

Here, the above HB-EGF precursor is, in other words, a membrane-bound type HB-EGF, and it is simply referred to "HB-EGF" in the following description.

F) A diabetes model animal set forth in any of A) to E), wherein the animal is a mouse or a rat.

Non-human mammals may be used as the diabetes model animal of the present invention, but among them the mouse and the rat are very commonly used as a laboratory animal and suitable as the diabetes model animal of the present invention, especially when the diphtheria toxin is used to induce a symptom of the diabetes, as mentioned above.

G) A method for generating the diabetes model animal set forth in F), comprising the steps of:
(a) constructing an expression unit comprising a gene (DNA) encoding a receptor for a compound, which is substantially non-toxic to a wild type of mouse or rat, under control of a promoter which functions specifically in islet beta cells;
(b) introducing this expression unit into a mouse or rat totipotent cell, such as a fertilized egg, an early embryo or an embryonic stem cell;
(c) transplanting thus obtained egg or embryo into an oviduct of a pseudopregnant female mouse (or rat); and
(d) selecting baby mice (or rats) having the above-mentioned gene (DNA) from born mice (or rats).

H) A method for screening new medicines or therapy protocols for diabetes, using the diabetes model animal set forth in any of A) to F), comprising the steps of:
(a) administrating test compounds (or transplanting test cells) into the diabetes model animal showing glycemia; and
(b) examining response of the animal, such as change of blood glucose level, blood insulin level, urine glucose level and survival rate, and then evaluating their effectiveness for diabetes.

Here, "new medicines" for diabetes include various biological materials, such as cells used for the Regenerative Medicine, and the present invention includes a method of evaluating effectiveness of such cells for the diabetes by transplanting them as a test material. The method includes all the analytical methods that may be useful in evaluation of a test material, such as histological examination, physiologic examination and behavior observation, as well as the examinations of blood glucose level, blood insulin level, urine glucose level and survival rate, as exemplified above.

EFFECT OF THE INVENTION

The diabetes model animal of the present invention has the following features and advantages, and it is useful as a tool for various researches such as the researches as to regeneration of the islet beta cells and identification of their stem cells. Furthermore, it is useful to the development of new treatment and therapeutic agent for the diabetes and the researches for its complications (other diseases caused by the diabetes).

(1) By administration of the diphtheria toxin, etc. at a desired time, it is possible to induce a symptom of the diabetes efficiently and rapidly (for example, about two or three days after the administration).
(2) It is possible to induce the diabetes with no male/female difference, and it enables to provide plural diabetes model animals for researches, with the same number of males and females.
(3) Because the receptor for the compound is expressed specifically in the islet beta cells, undesirable influences on any other organs or cells, and side reactions to them hardly happen.
(4) The damage to the islet beta cells can be controlled by adjusting dosage of the compound such as diphtheria toxin. It enables to provide different diabetes model animals, differing in some property such as the survival rate and/or the potential of restoration.
(5) In the diabetes model animal of the present invention, the islet beta cells express the receptor for the compound. Therefore, when the animal receives transplantation of islet beta cells or any other kinds of cells, the transplanted cells can be easily distinguished from the diabetes model animal's islet beta cells.

These and other objects, features and advantages of the present invention will become more apparent from the following description. Also, beneficial results of the present invention should be obvious from the following description when taken in conjunction with the accompanying drawings.

BEST MODE FOR CARRYING OUT THE INVENTION

Specific embodiments of the present invention are described in detail below with reference to the drawings.

Here, we explain the 1st and 2nd diabetes model mice as embodiments of the present invention, respectively described in Examples 1 and 2. Both are transgenic mice into which the human HB-EGF gene is introduced to express it specifically in the islet beta cells. The following is explanation of a method for producing these mice, including its modifications.

[1] Preparation of the Transgene (Expression Unit)

Figure 1:
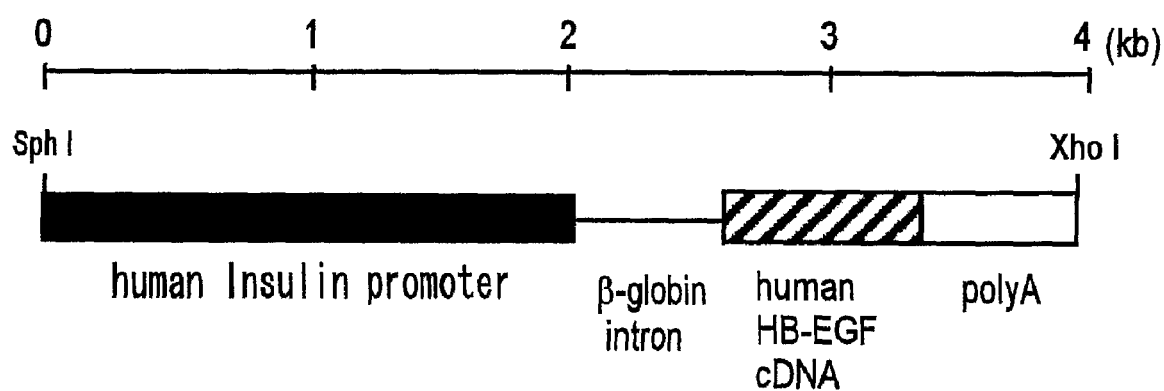
FIG. 1 schematically shows the structure of a transgene (expression unit) used for production of the first diabetes model mouse of the present invention.
Figure 9:
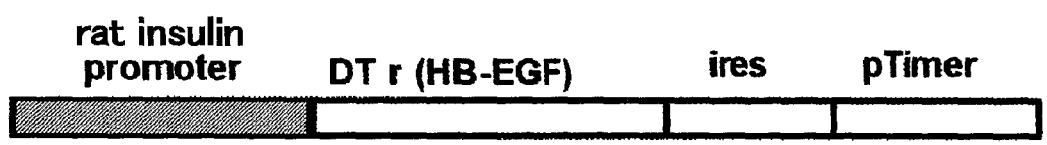
FIG. 9 schematically shows the structure of a transgene (expression unit) used for production of the second diabetes model mouse of the present invention.

FIGS. 1 and 9 show the schematic structures of the transgenes, respectively used for production of the 1st and 2nd diabetes model mice. The transgene used for production of the first diabetes model mouse has structure of "human insulin promoter—β-globin intron—human HB-EGF cDNA—β-globin polyA signal (polyA)" arranged in this order. In this structure, human HB-EGF cDNA is arranged in the downstream of human insulin promoter.

On the other hand, the transgene used for production of the second diabetes model mouse has structure of "rat insulin II promoter (rat insulin promoter)—β-globin intron (omission in FIG. 9)—human HB-EGF cDNA (DTr (HB-EGF), which is a diphtheria toxin receptor)—IRES (Internal Ribosome Entry Site)—PTimer (fluorescent protein whose color changing with the lapse of time, manufactured by Clontech Co.)—β-globin polyA signal (omission in FIG. 9)" arranged in this order. In this structure, human HB-EGF cDNA is arranged in the downstream of rat insulin promoter, not human insulin promoter. However, both transgenes are common in the structure of human HB-EGF cDNA arranged in the downstream of insulin promoter. By introducing a transgene with such structure into the mouse or other animal, human HB-EGF can be expressed specifically on the cell surface of the islet beta cells which are an insulin producing cell.

Generally, the transgene can be made by a known procedure (for example, see methods described in Molecular Cloning 2nd edition chapters 16 and 17, Cold Spring Harbor Laboratory Press). Also, as for the sequences of the human HB-EGF cDNA and the insulin promoters, etc., such sequences can be prepared on the basis of known sequence information (for example, see Cell Vol. 69, pp 1051-1061 (1992) and J. Exp. Med. Vol. 188, pp 1445-1451 (1998)).

[2] Production of the Diabetes Model Mice and Induction of a Symptom of the Diabetes Transgenic mice can be produced by introduction of a transgene with the above-mentioned structure into a mouse's fertilized egg or any other totipotent cells. Methods for producing transgenic mice normally include (1) a step of introducing the transgene into any of totipotent cells (having totipotency) such as a fertilized egg, an early embryo or an embryonic stem cell, (2) a step of transplanting thus obtained egg or embryo into an oviduct of a pseudopregnant female mouse, and (3) a step of selecting baby mice having the above transgene from born mice (for example, see "Experimental Medicine (Jikken Igaku Bessatsu) New Gene Engineering Handbook" revised 3rd edition, pp 234-238, Yodosha Co., Ltd., published on Sep. 10, 1999). Basically the 1st and 2nd diabetes model mice, described in the Examples below, were made in accordance with the above method.

As for the method of introduction of the transgene, the following methods are applicable; a method of directly injecting the transgene into the pronucleus of a fertilized egg by use of a micropipette under a differential interference contrast microscopy (microinjection; Proc. Natl. Acad. Sci. USA 77, 7380-7384 (1980)), a method using a recombinant retrovirus vector (retrovirus method; Proc. Natl. Acad. Sci. USA 82, 6148-6152, 6927-6931, 8587-8591 (1985)), and a method using an embryonic stem cell (ES cell) (Proc. Natl. Acad. Sci. USA 83, 9065-9069 (1986)). In these methods, transgenic mice can be generated by, for example, harvesting fertilized eggs, injecting the transgene into the pronuclei of the eggs using a micromanipulator, and then transplanting the obtained eggs into a uterine tube. Alternatively, transgenic mice can be generated by introducing the transgene into an ES clone by electroporation, selecting desired cells in terms of drug resistance, injecting the selected cells into fertilized eggs using a micromanipulator to create chimera embryos.

Figure 2:
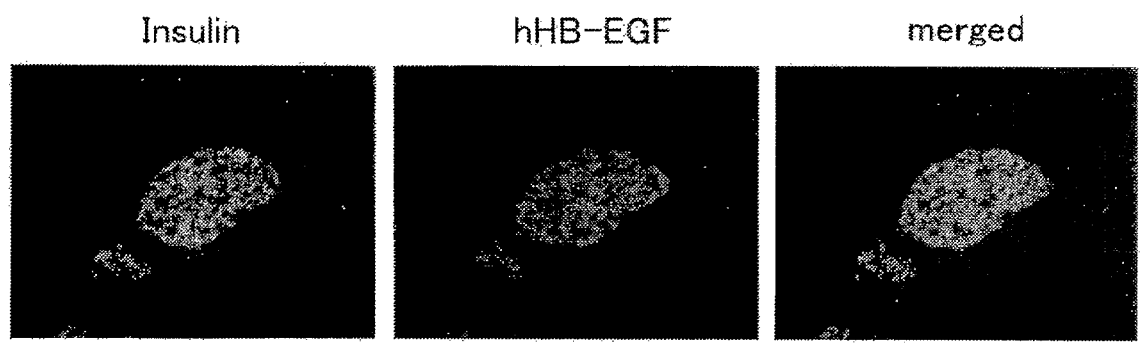
FIG. 2 is a photograph showing specific expression of the human HB-EGF in the islet beta cells, which are an insulin producing cell, of the first diabetes model mouse.
Figure 3:
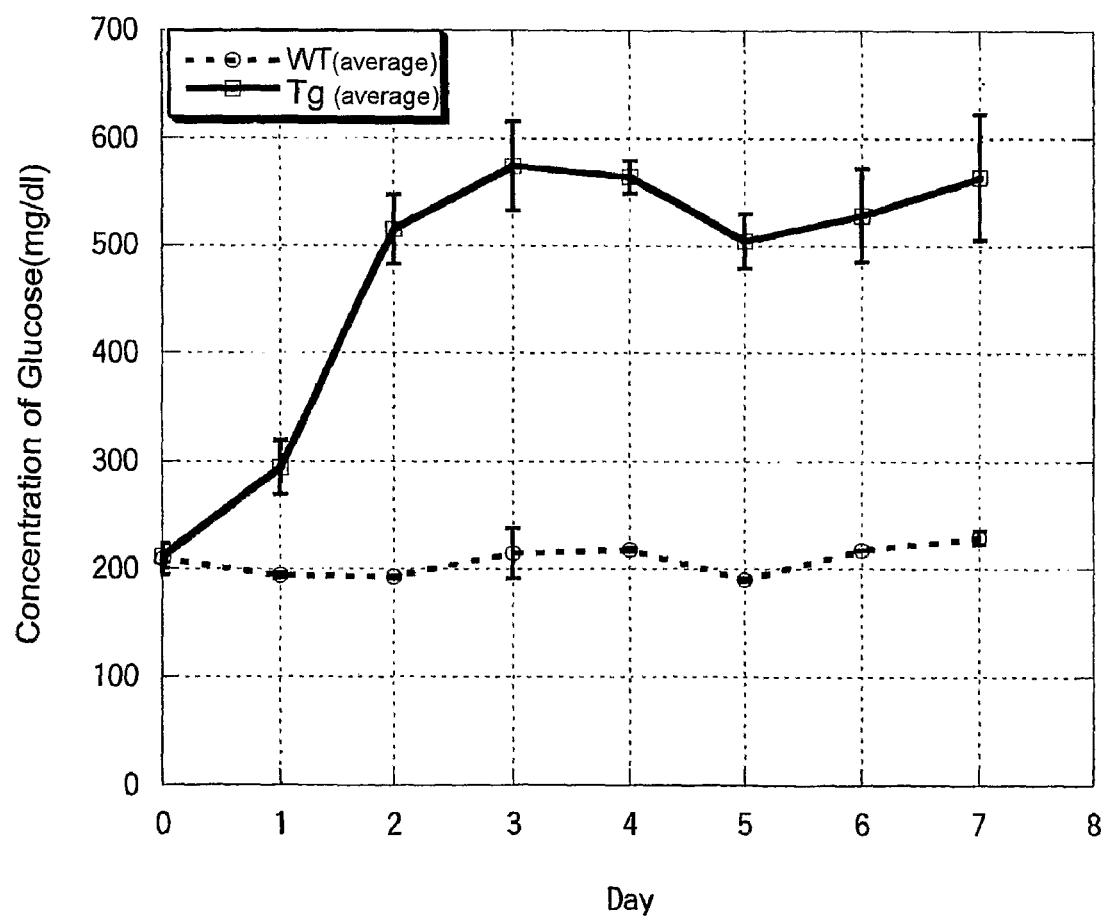
FIG. 3 is a graph showing that the blood glucose level of the first diabetes model mouse increased by administration (injection) of the diphtheria toxin. In the graph, solid line represents a result of the first diabetes model mouse, while broken line represents a result of the wild type mouse.
Figure 4:
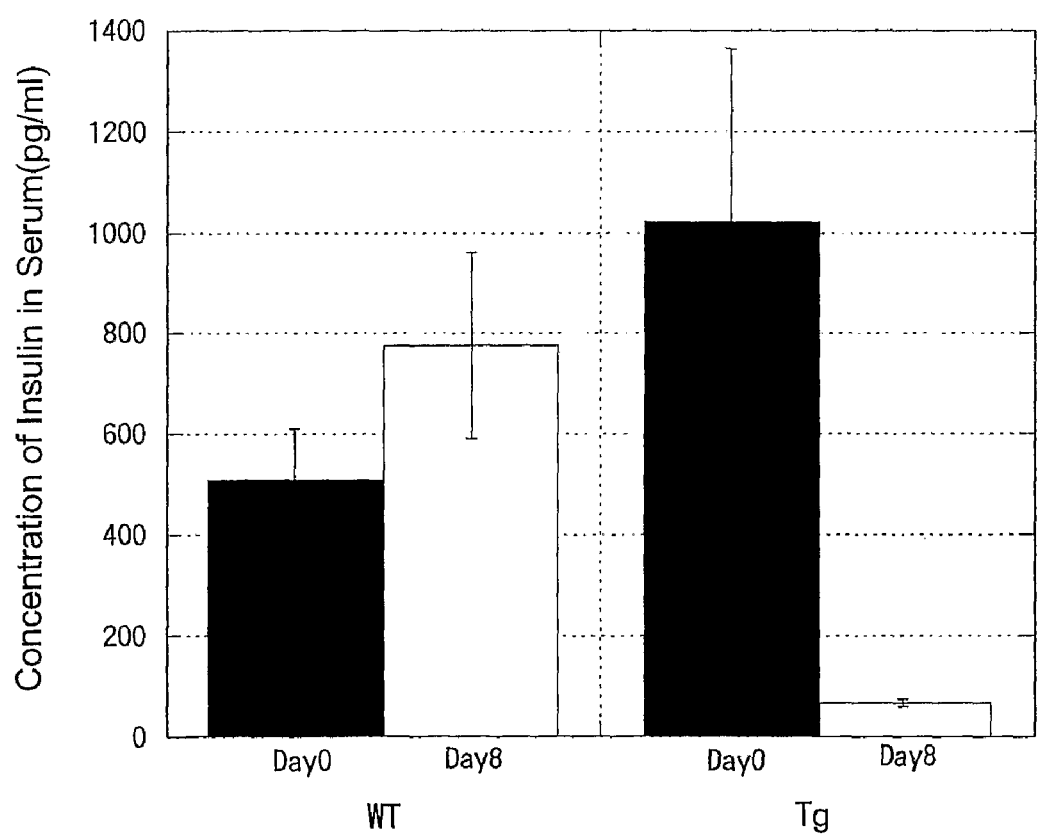
FIG. 4 is a graph showing that the blood insulin level of the first diabetes model mouse remarkably decreased by administration of the diphtheria toxin. In the graph, "Tg" on the right side represents a result of the first diabetes model mouse, while "WT" on the left side represents a result of the wild type mouse.
Figure 5:
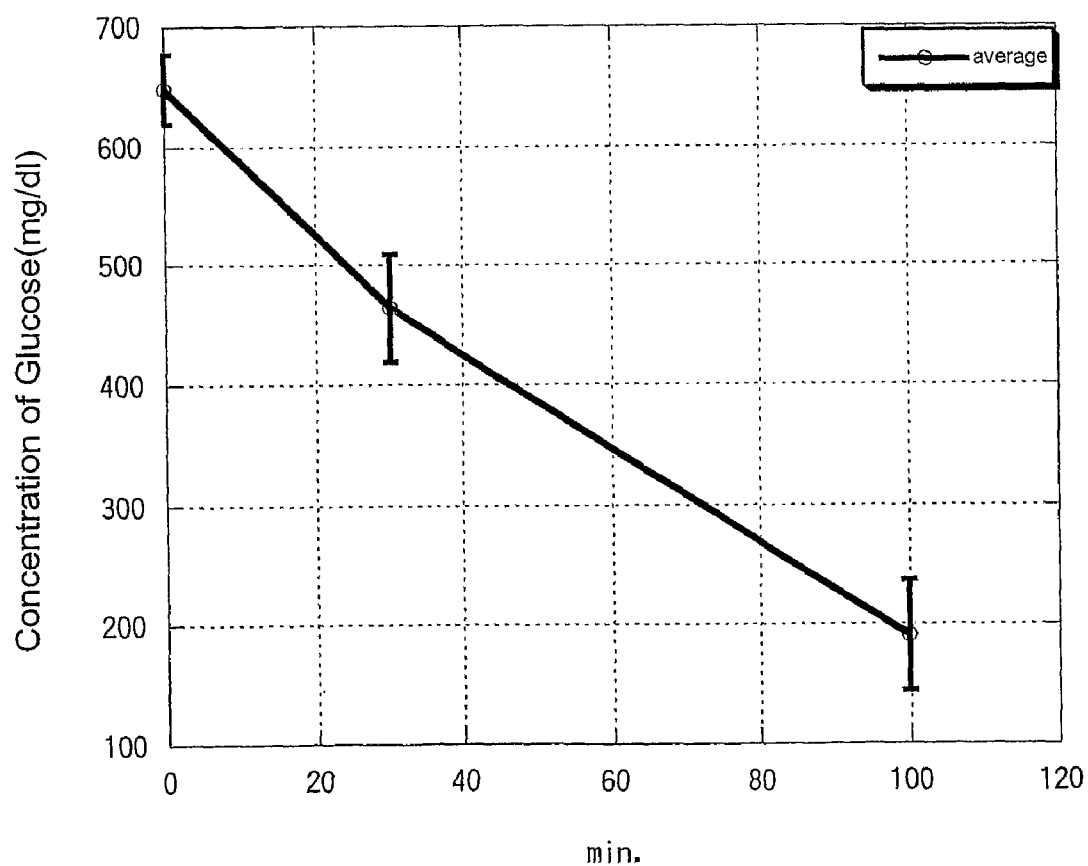
FIG. 5 is a graph showing that the blood glucose level of the first diabetes model mouse decreased down to the same level as that of the wild type mouse, by administration of the insulin.
Figure 6:
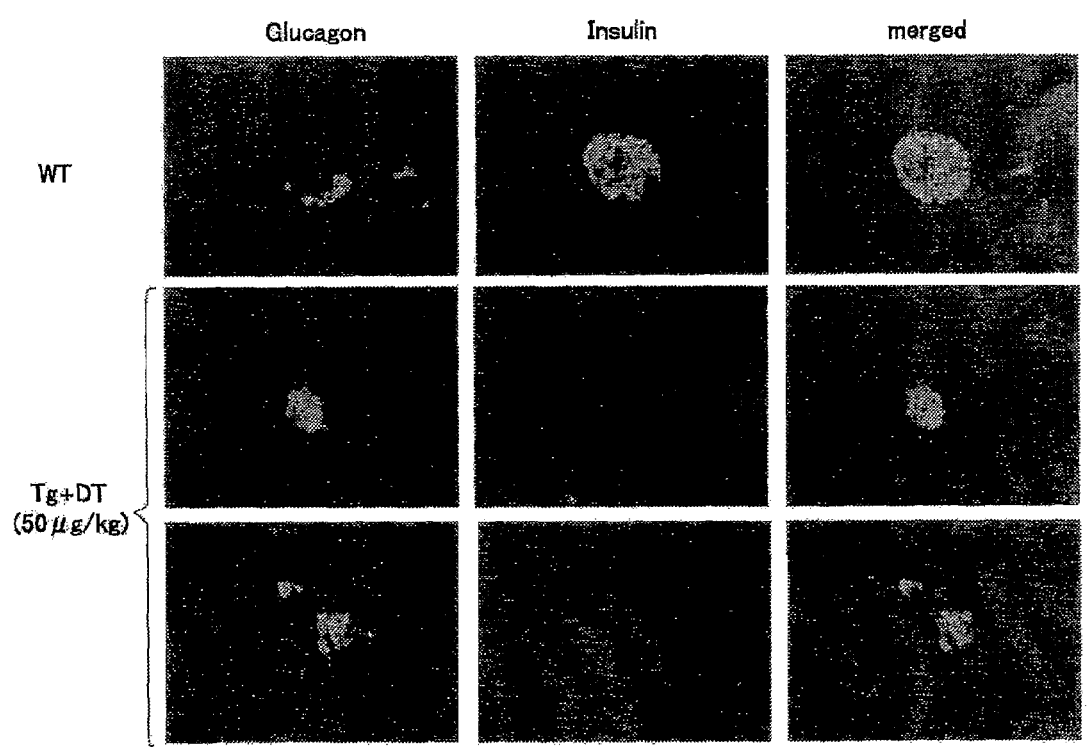
FIG. 6 is a photograph showing that the islet beta cells of the first diabetes model mouse were destroyed after the diphtheria toxin was administered (injected) in the proportion of 50 μg/kg (middle and lower panels), as a result of immunostaining study. The upper panel shows a result of the wild type mouse into which the same proportion of diphtheria toxin was administered.
Figure 10:
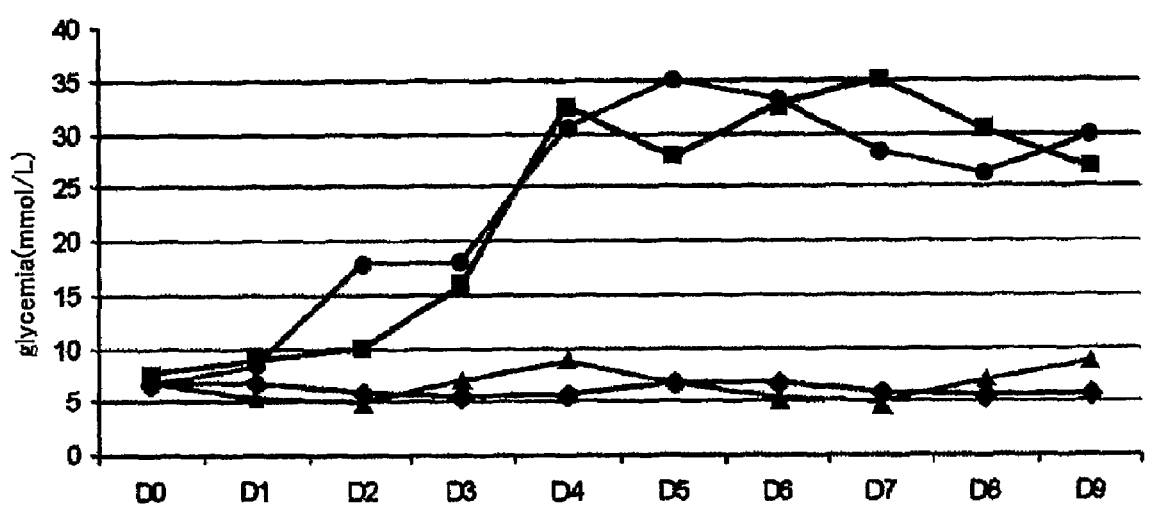
FIG. 10 is a graph showing that after administration of the diphtheria toxin into the second diabetes model mice, the blood glucose level (glycemia) (mmol/L) increased in the two lines of mice (shown by the symbols of circle and square). Note that the other two strains (Tg(-)) remained insensitive to the diphtheria toxin. The graph shows a result from the day of administration (D0) to the ninth day (D9).
Figure 11:
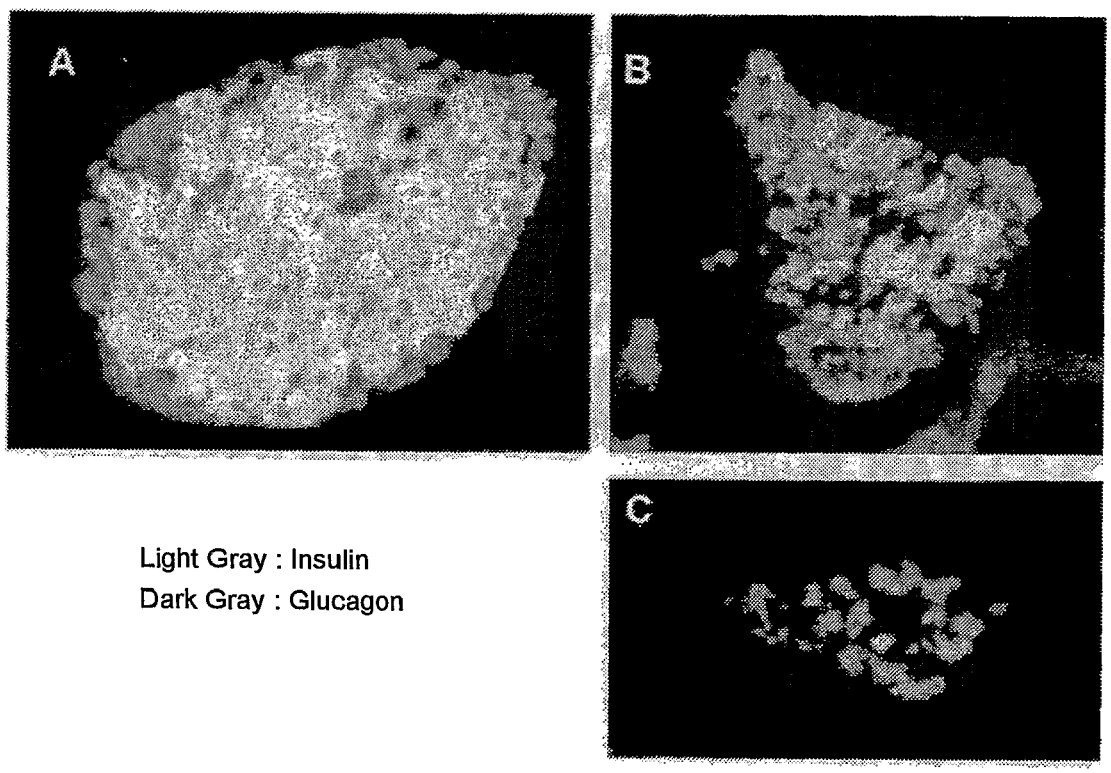
FIG. 11 is a photograph showing that the islet beta cells of the second diabetes model mouse were destroyed after the diphtheria toxin was administered (B·C), as a result of immunostaining study. "A" shows a result of immunostaining study for the islet of the littermate, into which no diphtheria toxin was administered.

The transgenic mouse generated by the above method, in fact, had the human HB-EGF expressed specifically in the islet beta cells which are insulin producing cells (FIG. 2). Moreover, the transgenic mouse clearly showed a symptom of hyperglycemia two or three days after administration of the diphtheria toxin (FIG. 3 and FIG. 10). After the administration, the insulin concentration in blood remarkably decreased, as compared with the wild type mouse (FIG. 4). Histological analysis revealed that only the islet beta cells were selectively destroyed (FIG. 6 and FIG. 11). Additionally, after insulin was administrated, the blood glucose level was restored to a normal level (FIG. 5).

Thus, the diabetes model mouse of the present invention express the diphtheria toxin receptor specifically in the islet beta cells, so that those cells can be selectively destroyed by a single-dose of the diphtheria toxin. Before the administration, the diabetes model mice are apparently normal, but they show a symptom of the diabetes (i.e., hyperglycemia and/or hypoinsulinism), promptly after administration of the diphtheria toxin. Moreover, neither abnormalities nor side reactions were observed in any other organs and cells than the islet beta cells.

Figure 8:
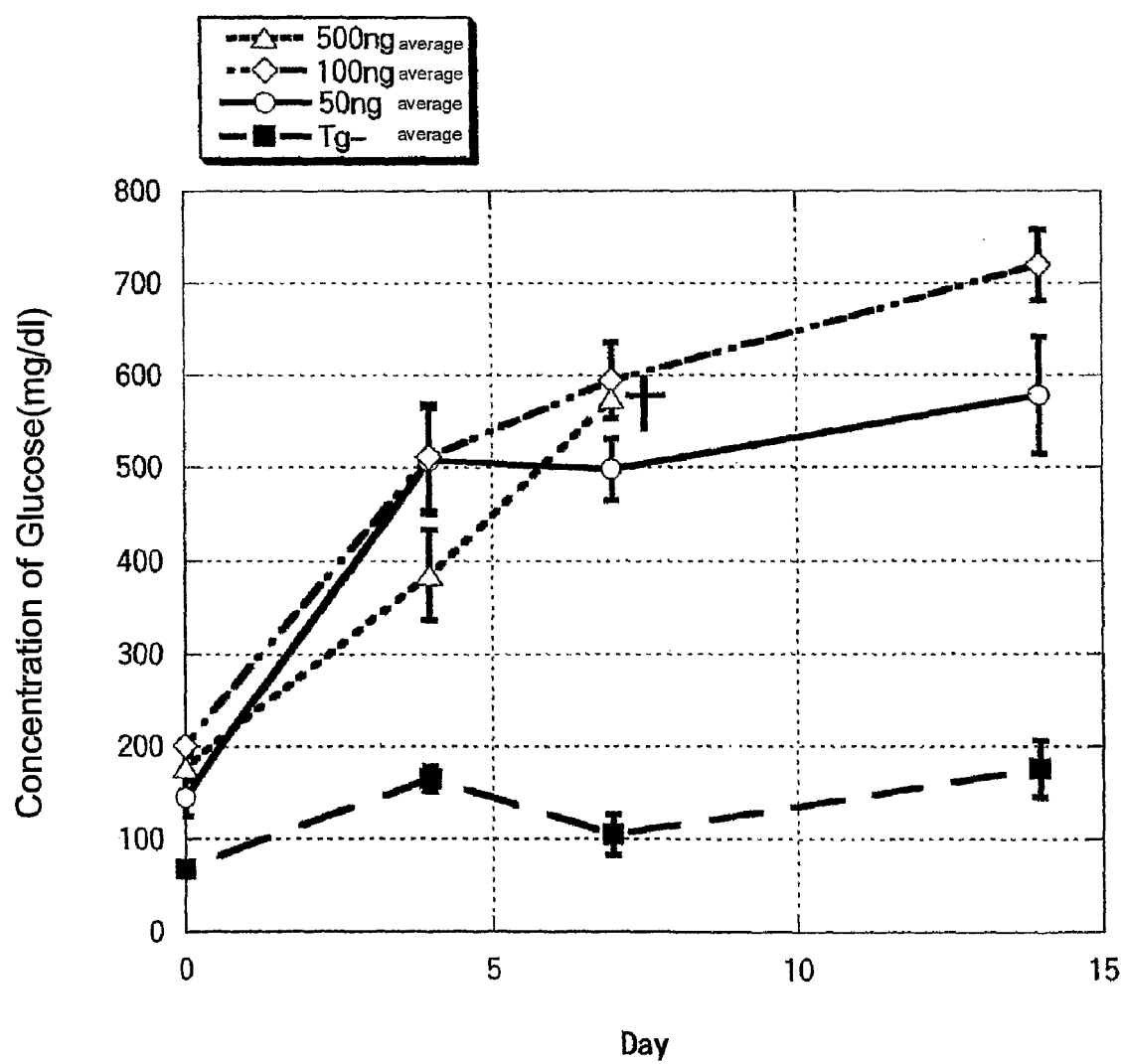
FIG. 8 is a graph showing changes of the blood glucose level after various dosages (amounts) of diphtheria toxins were administered to the first diabetes model mouse. "Tg-" shows a result of the mouse, into which no transgenes were introduced, having diphtheria toxin administered in the proportion of 500 mg/kg (body weight).

The method of administrating the diphtheria toxin is not especially limited, although non-oral dose, such as the intravenous injection or the intraperitoneal injection, is preferable. The symptom of the diabetes was able to be induced efficiently and promptly by administrating a low amount of the diphtheria toxin, i.e., in the amount (proportion) of about 50 ng/kg (body weight) (FIG. 8). Taking into consideration that the wild type mice are non-sensitive to the diphtheria toxin and they have little influence even if 1000 times higher amount (i.e., 50 µg/kg) of the diphtheria toxin are administrated to them, it is surprisingly that the diabetes model mouse of the present invention is highly sensitive to the diphtheria toxin and it responds to the toxin promptly after administration of a low amount of the toxin, showing a symptom of the diabetes.

Moreover, it was found that survival rates of the diabetes model mice were different according to the dosage (amount) of the diphtheria toxin (FIG. 7) and the mice were survivable for a long term when they received the dosage of the toxin in the amount of about 100 ng/kg or less. It is desirable that the model mouse can live for a long term, and therefore the diabetes model mouse of the present invention is excellent because it shows hyperglycemia by a low amount of the toxin and survivable for a long term.

Figure 7:
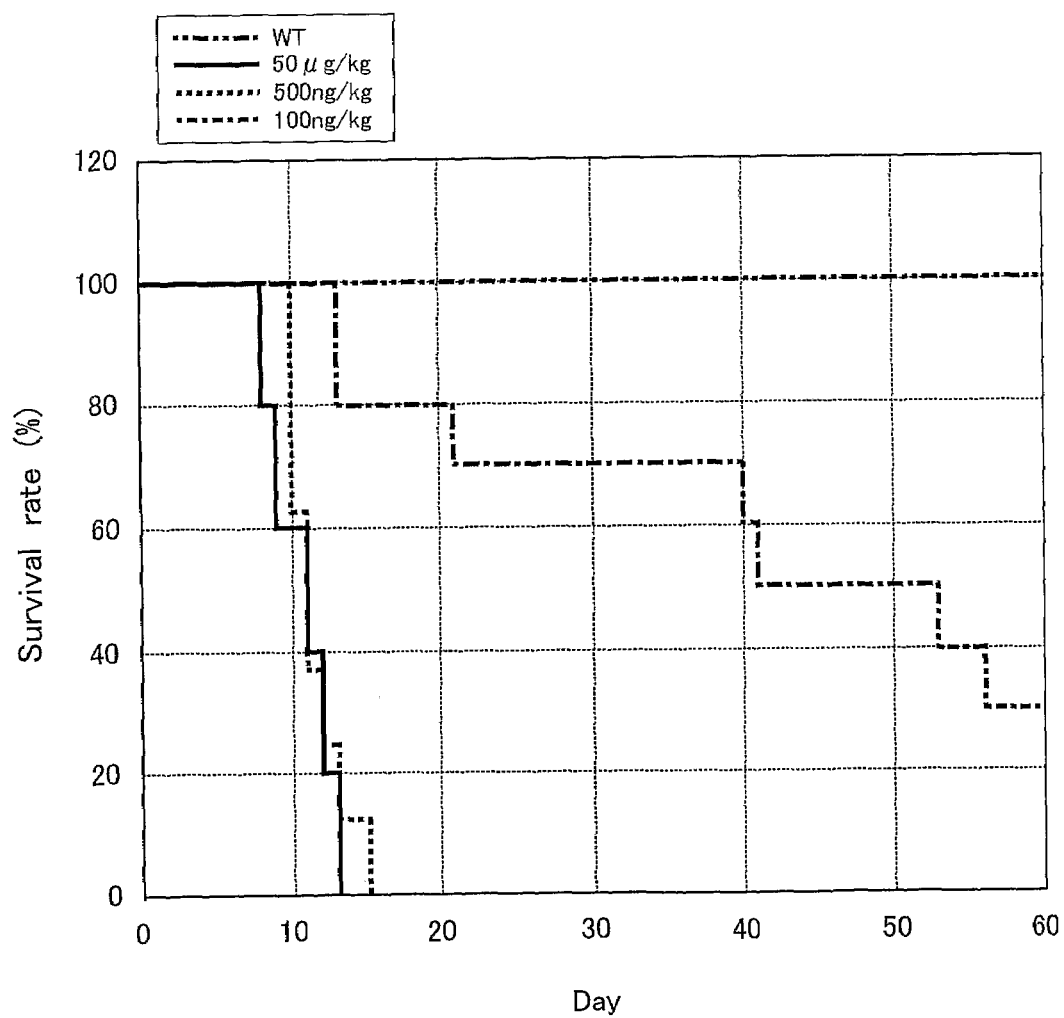
FIG. 7 is a graph showing survival rates after various dosages (amounts) of diphtheria toxins were administered to the first diabetes model mice. "WT" shows a result of the wild type mouse into which diphtheria toxin was administered in the proportion of 50 μg/kg (body weight).

When the diphtheria toxin of 50 µg/kg and 500 ng/kg was administrated to the transgenic mice, all the mice died in a short term (about ten days after the administration) (FIG. 7). Of course, even if the transgenic mice exhibited a symptom of the diabetes by such dosage, they can be also useful as a diabetes model mouse, and when an effective test compound or insulin is administrated into them, they can live for a long term.

As mentioned above, it is thought that the difference in the survival rates among the diabetes model mice is caused by the dosage of the diphtheria toxin because the destruction ratio or level of the islet beta cells is different according to the dosage of the diphtheria toxin. In other words, a variety of diabetes model mice can be provided by adjusting the dosage of the diphtheria toxin, because they are different in the destruction ratio of the islet beta cells, the survival rate and the potential of restoration, etc. according to the dosage. Moreover, it is possible to induce a symptom of the hyperglycemia by a single-dose of the diphtheria toxin. Of course, it is also possible to administrate (inject) a low amount of the toxin several times, in order to gradually destroy the islet beta cells and make the model mouse live for a long term, for example when the regenerative effect due to cell transplantation is examined.

[3] Some Modifications of the Diabetes Model Mice Mentioned Above (1) By a known procedure, you may modify or change one or several bases within the original sequence of the human HB-EGF gene and then introduce thus artificially modified gene into the cell or embryo of a target animal. Such modification includes substitution, deletion, insertion and addition of one or several bases. For instance, it is a preferred approach to prepare one modified gene encoding a human HB-EGF having an improved binding ability with the toxin, and then introduce such gene into the cell or embryo of a target animal. Alternatively, you may prepare another modified gene encoding a human HB-EGF, whose growth factor function is lost but its binding ability with the toxin is maintained.

(2) Instead of use of the human HB-EGF gene as a diphtheria toxin receptor gene, it is possible to use different HB-EGF genes derived from other kinds of animals such as the ape.

(3) "A compound, which is substantially non-toxic to a wild type of the animal" of the present invention is not limited to the diphtheria toxin, but includes toxins derived from other bacteria, such as the *Pseudomonas aeruginosa*, the *Bordetella pertussis*, the *Vibrio cholerae* and the *Clostridium botulinum*. However, model animals should be selected among kinds of animals with low sensibility (receptivity) for the toxin used as "a compound". For instance, when the *Pseudomonas aeruginosa*'s exotoxin is used, model animals other than the rat and the mouse should be selected, because the *Pseudomonas aeruginosa*'s exotoxin shows a strong toxicity to the rat and the mouse. In the case of using a toxin other than the diphtheria toxin, one can adopt the method that makes a receptor for the toxin express specifically onto the surface of the islet beta cell of a target animal, like the above-mentioned method in the case of using the diphtheria toxin.

(4) The model animal is not limited to the mouse but also includes a variety of animals such as the rat, the guinea pig, the hamster, the bos taurus, the pig, the sheep, the goat, the rabbit and the ape. However, as mentioned above, model animals should be selected among kinds of animals with low sensibility (receptivity) for the toxin used as "a compound" to induce a symptom of the diabetes.

[4] Industrial Applicability (Utility) of the Diabetes Model Animal of the Present Invention As mentioned above, the diabetes model animal of the present invention can be utilized in the development of new medicines and therapy protocols for the diabetes. For instance, after a test material (a compound or a biological material (such as cell or tissue)) is administrated (or transplanted) to the diabetes model animal already showing a symptom of the induced hyperglycemia, then the animal can be utilized in various experiments and examinations, including the examinations relating to change of blood glucose level, blood insulin level, urine glucose level and survival rate, in order to evaluate effectiveness of the test material for the diabetes. The diabetes model animal of the present invention makes the search for an effective material much easier, and thus it is very useful for the development of the medicines and foods, effective for the diabetes.

New treatment for the diabetes is recently attempted; transplantation regenerative treatment to regenerate the islet beta cells through transplantation such as islet transplantation. The diabetes model animal of the present invention can be utilized in the research and development for this transplantation regenerative treatment. For example, the animal can be used as a recipient, to which various cells (or tissue) such as the bone marrow cells, the spleen cells and the cord blood derived cells, are administrated in order to evaluate regeneration of the islet beta cells by them. The diabetes model animal of the present invention makes such evaluation much easier, because regenerated islet beta cells are resistant to the used toxin, which is one of the benefits of the present invention.

The search for the stem cell of the islet beta cells is important for the development of the transplantation regenerative treatment. The diabetes model animal of the present invention can be also utilized in such search for the stem cell. For example, after the diphtheria toxin is administrated to the model animal in the fetal or adult period, in order to destroy its islet beta cells, the animal can be used for the observation and evaluation of regeneration of the islet beta cells by endogenous stem cells.

Moreover, it is possible to efficiently produce a complication model from the diabetes model animal of the present invention, and thus it can be used for the researches of various complications, caused by the diabetes, such as diabetic neuropathy, diabetic hypertonias and diabetic arteriosclerosis, in addition to diabetic blindness and urinemia, and for the development of new treatment of such complications. In addition, it is useful as a tool for the research that investigates the relationship between the diabetes and relevant factors, such as obesity, shortage of physical activity and mental stresses.

EXAMPLES

The present invention is described in detail below through two Examples thereof, as to the 1st and 2nd diabetes model mice, but in no way is the present invention limited to these Examples.

Example 1

Production and Function Analysis of the First Diabetes Model Mouse

[1] Method

[1-1] Construction of a Transgene for Production of the Transgenic Mouse

For preparation of the transgene (expression unit), human HB-EGF cDNA was cut out from the plasmid pRcHBEGF (EMBO J. 13, 1994, 2322-2330) by the restriction enzymes Hind III-Not I, and it was made to have the blunt end by using DNA Blunting Kit (TaKaRa). Then, the human HB-EGF cDNA was inserted (at Eco RI site) in the downstream of human insulin promoter (1.9 kb), within the plasmid pIns-1 (J. Exp. Med. Vol. 188, Oct. 19, 1998, 1445-1451), to obtain the plasmid pIns-TR1.

The fragment of 3.8 kb was cut out from the above plasmid pIns-TR1 by the restriction enzymes Sph I-Xho I, which was purified by use of QIAquick Gel Extraction Kit (QIAGEN) and then used as the transgene (FIG. 1).

[1-2] Production of the Transgenic Mouse

The above transgene was introduced into fertilized eggs obtained from C57BL/6J Jcl×C57BL/6J. Jcl. Then, the fertilized egg was transplanted to an oviduct of the recipient mouse (ICR Jcl), in order to produce the transgenic mouse. The transgenic mouse was identified by the PCR analysis using the following primers, corresponding to the sequences between which the human insulin promoter and the human HB-EGF cDNA are sandwiched.

```
Forward primer Ins-F001:
5'-tgcctgtctcccagatcactgtg-3'      (SEQ NO. 1)

Reverse primer HBEGF-30R:
5'-ttcagcaccaccgacggcagca-3'       (SEQ NO. 2)
```

[1-3] Expression Analysis of Human HB-EGF in the Transgenic Mouse

The transgenic mouse was anesthetized by the pentobarbital, and then perfusion fixation was performed using 4% paraformaldehyde. After over night postfixation using the same fixation solution, it was replaced by 30% sucrose. After frozen with the Cryomold (Sakura Finetechnical Co. Ltd), the sections with 10 µm thickness were prepared using the cryostat.

The incubation was carried out for two hours at the room temperature, in the case of the primary antibodies (Goat anti-HB-EGF (GT, 1000 times dilution), Rabbit anti-Glucagon (Dako, 100 times dilution), and Guinea Pig anti-Insulin (DAKO, 200 times dilution)), while the incubation was carried out for one hour at the room temperature in the case of the secondary antibodies (Jackson). In the case of the double staining mentioned below, the incubation was carried out alike after washing, with the primary antibodies and then the secondary antibodies. After washed with PBS, the sections were embedded in VECTASheild with DAPI (Vector), and then observed.

[1-4] Measurement of the Blood Glucose Level and the Insulin Concentration

The mouse's caudal vein was cut out with a razor, and the blood glucose level was measured using Glucocard diametar (ARKRAY). Alternatively, the blood glucose level was measured with Glucose CII-TestWaco (mutarotase, GOD method) (Wako Pure Chemical Industries, Ltd.) from the mouse's serum, which was obtained by the centrifugation of 5000 rpm, 5 minutes at 4° C., for the blood samples collected from the tail or the eye socket. The insulin concentration was measured using insulin measuring kit (MORINAGA).

[1-5] Insulin Tolerance Test

Insulin (Humulin R U-100, Eli Lilly Japan) solution was intraperitoneally administrated at the 2 U/kg, and then blood samples were collected at 0, 30 and 100 minutes respectively.

[2] Result

[2-1] Production of the Transgenic Mouse and Expression of Human HB-EGF

The transgenes of 1.5-2 ng/µl were respectively injected in 1009 fertilized eggs and 81 mice were obtained. After weanling, each mouse's DNA was collected from the tail and the PCR analysis was performed, which revealed that the transgene was introduced into eight mice (five females, three males). Among these mice, two lines were established. To confirm expression of the human HB-EGF in these mice, immunohistochemical staining for their pancreas was performed using the human anti-HB-EGF antibody. Furthermore, we performed the double staining together with the anti-insulin antibody, to examine specific expression of the human HB-EGF in the islet beta cells, which demonstrated that one line (named "6F6") of two lines had specific expression of the human HB-EGF, where the human HB-EGF was coexpressed with the insulin in the insulin positive cells (FIG. 2).

[2-2] Elevation of the Blood Glucose Level, Caused by Administration of the Diphtheria Toxin The above-mentioned line "6F6" was used in the following experiments. The diphtheria toxin was administrated into the mouse of this line "6F6". Generally, a wild type mouse dies by a dosage of the diphtheria toxin in the amount of about 500 μg/kg (body weight), because of incorporation of the toxin in a non-receptor-depending manner. However, a wild type mouse has little influence by a dosage in its 1/10 amount (50 μg/kg) of the toxin. Here, the diphtheria toxin was intraperitoneally administrated (injected) to the transgenic mouse in the amount of 50 μg/kg, for which a wild type mouse has little influence. Administration (injection) was carried out on around 11:00 AM of a day, and blood samples were collected from the eye socket just before the administration. Blood samples were also collected between 11 o'clock and 13 o'clock every day after the day. The serum was prepared from the blood samples, and the blood glucose level and the insulin concentration were measured. As for the blood glucose level, it began to clearly increase during the second day, and on the third day the blood glucose level exceeded 500 mg/dl in all of the five transgenic mice into which the toxin was administrated (FIG. 3).

After the diphtheria toxin was administrated, the transgenic mice became polyuria, and their urinary sugar values also increased. Moreover, their hair's appearance got worse. In the transgenic mice, the insulin concentration decreased down to 100 pg/ml or less on the eighth day (FIG. 4).

[2-3] Decrease of the Blood Glucose Level Due to Administration of the Insulin

The insulin tolerance test was carried out for the mice, whose blood glucose level increased by administration of the diphtheria toxin in the amount of about 50 μg/kg, in order to examine whether the increase of the blood glucose level in the transgenic mice is insulin-dependent or not. In the test, the insulin (Humulin R 100) of 2 U/kg was intraperitoneally administrated to the mice, and blood samples were collected in 0, 30 and 100 minutes respectively (0 minutes means just before the insulin administration), and the blood glucose level was measured. The result was that the blood glucose level decreased in all of the mice down to the level of about 200 mg/dl (FIG. 5). Its level was almost the same as that of the wild type mouse.

[2-4] The Destruction of the Islet Beta Cells

Ten days after the toxin administration, the mouse was fixed with formalin, followed by the immunostaining with the anti-insulin (for the beta cells) and the anti-glucagon (for the alpha cells). In the diabetes model mouse "Tg (+)" of the present invention, into which the transgene was introduced, the number of the insulin positive cells clearly decreased by administration of the diphtheria toxin of 50 μg/kg (FIG. 6). On the other hand, in the mouse "Tg (−)" into which the transgene was not introduced, the staining images showed the same tendency as those of the wild type mouse, even after administration of the toxin.

[2-5] Study of the Survival Rates for Various Dosages of the Toxin

The toxin was administrated to the diabetes model mouse of the present invention in the various dosages, i.e., in each level of 50 μg/kg, 500 ng/kg and 100 ng/kg, in order to study the survival rate for each level. In this study, five males and five females were used, to examine whether or not there is any male/female difference.

As a result, as shown in FIG. 7, all the mice died in the 10-12th day after administration in the amount of 50 μg/kg, while all the mice died in the 10-15th day after administration in the amount of 500 ng/kg.

Two in ten mice died on the 15th day after administration of the toxin in the amount of 100 ng/kg, and five mice died, one by one, on each day of the 21st, 40th, 41st, 53rd and 56th days. The remaining three mice lived for two months or more in the state of the hyperglycemia, the hyperglycosuria and the polyuria.

After the toxin was administrated to the diabetes model mouse of the present invention in each level of 500 ng/kg, 100 ng/kg and 50 ng/kg, their blood glucose level was examined in each group of mice. The result is shown in FIG. 8.

In the 50 ng/kg toxin administrated group, the blood glucose level rose in the 2nd-3rd day after administration, as well as other groups. The high level of blood glucose was maintained for a while, but when one and a half months passed, the blood glucose level and the urinary sugar level recovered to almost the same level as that of the normal mouse. Since then, no mice died for two months.

Example 2

Production and Function Analysis of the Second Diabetes Model Mouse

The transgene used for production of the second diabetes model mouse is shown in FIG. 9. The transgene has structure of "rat insulin II promoter (about 600 bp)—rabbit beta-globin intron (omission in FIG. 9)—human HB-EGF cDNA—IRES—PTimer—rabbit beta-globin polyA signal (omission in FIG. 9)" arranged in this order.

Using the above transgene, the transgenic mouse was made according to a known procedure as discussed above. As a result, seven lines of mice having the sequence of the above transgene were obtained. After the diphtheria toxin was intraperitoneally administrated into two lines of mice among these mice in a single-dose of 250 ng, the blood glucose level clearly increased in these two lines of mice in the 2nd-3rd day after the administration (FIG. 10). Then, the state of the hyperglycemia continued over several weeks. In the mice where the blood glucose level increased, various symptoms such as polyuria, glycosuria, hyperphagia, polydipsia and cachexia were observed, which are often seen in the juvenile diabetes (Type 1 diabetes mellitus). After that, the mice died soon.

The histological observation revealed that the number of the insulin positive cells decreased remarkably in the islet of pancreas, after the diphtheria toxin was administrated to the second diabetes model mouse, and thus selective destruction of the islet beta cells was observed (FIG. 11B C).

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

INDUSTRIAL APPLICABILITY

As discussed above, the present invention relates to an inducible diabetes model animal, whose islet beta cells can be selectively destroyed by administration of a compound such as a diphtheria toxin, so that it is possible to induce a symptom of the diabetes at a desired time in the animal, which can be utilized as a tool for various researches such as the researches as to regeneration of the islet beta cells and identification of their stem cells. The diabetes model animal of the present invention can be also utilized in the development of new medicines and therapy protocols for the diabetes and its complications, thus having a variety of industrial applicability.

The invention claimed is:

1. A transgenic mouse whose genome comprises a nucleic acid sequence encoding a diphtheria toxin receptor operably linked to an insulin promoter that causes expression specifically in islet beta cells, wherein the diphtheria toxin receptor is expressed specifically in islet beta cells of the mouse such that the mouse shows hyperglycemia when diphtheria toxin is administered to the mouse, and wherein the islet beta cells are selectively disrupted when diphtheria toxin is administered to the mouse.

2. The transgenic mouse of claim 1, wherein the diphtheria toxin receptor is a human heparin-binding EGF-like growth factor (hHB-EGF) precursor, and wherein at least 50 ng of diphtheria toxin has been administered to the mouse.

3. A transgenic mouse whose genome comprises a nucleic acid sequence encoding a diphtheria toxin receptor operably linked to an insulin promoter that causes expression specifically in islet beta cells, wherein the diphtheria toxin receptor is expressed specifically in islet beta cells of the mouse, and wherein diphtheria toxin is administered to the mouse such that islet beta cells of the mouse are selectively disrupted and wherein the mouse shows hyperglycemia.

4. A method of generating a transgenic mouse, comprising the steps of:

(a) constructing a nucleic acid sequence encoding a diphtheria toxin receptor operably linked to an insulin promoter that functions specifically in islet beta cells;

(b) introducing the nucleic acid sequence into a fertilized mouse embryo or a mouse ES cell;

(c) transplanting the fertilized mouse embryo or a mouse ES cell obtained in step (b) to a recipient female; and (d) selecting an offspring that contains the nucleic acid sequence.

* * * * *